(12) United States Patent
Rockley

(10) Patent No.: US 10,342,701 B2
(45) Date of Patent: Jul. 9, 2019

(54) SYSTEMS AND METHODS FOR PHACOEMULSIFICATION WITH VACUUM BASED PUMPS

(75) Inventor: Paul Rockley, Corona Del Mar, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 463 days.

(21) Appl. No.: 11/837,980

(22) Filed: Aug. 13, 2007

(65) Prior Publication Data

US 2009/0048607 A1 Feb. 19, 2009

(51) Int. Cl.
*A61F 9/007* (2006.01)
*A61M 1/00* (2006.01)

(52) U.S. Cl.
CPC ....... *A61F 9/00745* (2013.01); *A61M 1/0031* (2013.01); *A61M 1/0058* (2013.01); *A61M 2205/8206* (2013.01); *A61M 2210/0612* (2013.01)

(58) Field of Classification Search
CPC A61F 9/00745; A61M 1/0031; A61M 1/0058
USPC ............................ 623/1.12; 604/22; 606/107
See application file for complete search history.

(56) References Cited

U.S. PATENT DOCUMENTS

| | | |
|---|---|---|
| 1,848,024 A | 3/1932 | Owen |
| 2,123,781 A | 7/1938 | Huber |
| 2,990,616 A | 7/1961 | Balamuth et al. |
| 3,076,904 A | 2/1963 | Claus et al. |
| 3,116,697 A | 1/1964 | Bilichniansky |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,247,784 A | 1/1981 | Henry |
| 4,276,023 A | 6/1981 | Phillips et al. |
| 4,286,464 A | 9/1981 | Tauber et al. |
| 4,537,561 A | 8/1985 | Xanthopoulos |

(Continued)

FOREIGN PATENT DOCUMENTS

| | | |
|---|---|---|
| AU | 2006235983 A1 | 5/2007 |
| CA | 2662797 A | 3/2008 |

(Continued)

OTHER PUBLICATIONS

"Phacoemulsification. Oct. 12, 2006. Wikipedia.com. Jun. 19, 2009 http://en.wikipedia.org/wiki/Phacoemulsification,".

(Continued)

*Primary Examiner* — Kathleen S Holwerda
*Assistant Examiner* — Sarah A Simpson
(74) *Attorney, Agent, or Firm* — Johnson & Johnson Surgical Vision, Inc.

(57) ABSTRACT

The invention is generally directed to systems and methods for ophthalmic surgery, and more particularly to systems and methods for phacoemulsification using vacuum-based aspiration pumps. In accordance with one embodiment, a vacuum-based phacoemulsification system, having a handpiece, includes a subsystem to detect an occlusion occurring at the handpiece during operation.

7 Claims, 5 Drawing Sheets

(56) References Cited

U.S. PATENT DOCUMENTS

| | | | |
|---|---|---|---|
| 4,564,342 | A | 1/1986 | Weber et al. |
| 4,590,934 | A | 5/1986 | Malis et al. |
| 4,662,829 | A | 5/1987 | Nehring |
| 4,665,621 | A | 5/1987 | Ackerman et al. |
| 4,706,687 | A | 11/1987 | Rogers et al. |
| 4,713,051 | A | 12/1987 | Steppe et al. |
| 4,757,814 | A | 7/1988 | Wang et al. |
| 4,758,220 | A | 7/1988 | Sundblom et al. |
| 4,758,238 | A | 7/1988 | Sundblom et al. |
| 4,772,263 | A | 9/1988 | Dorman et al. |
| 4,773,897 | A | 9/1988 | Scheller et al. |
| 4,818,186 | A | 4/1989 | Pastrone et al. |
| 4,819,317 | A | 4/1989 | Bauer et al. |
| 4,837,857 | A | 6/1989 | Scheller et al. |
| 4,920,336 | A | 4/1990 | Meijer |
| 4,921,477 | A | 5/1990 | Davis |
| 4,925,444 | A | 5/1990 | Orkin et al. |
| 4,933,843 | A | 6/1990 | Scheller et al. |
| 4,941,518 | A | 7/1990 | Williams et al. |
| 4,954,960 | A | 9/1990 | Lo et al. |
| 4,961,424 | A | 10/1990 | Kubota et al. |
| 4,965,417 | A | 10/1990 | Massie |
| 4,983,901 | A | 1/1991 | Lehmer |
| 4,998,972 | A | 3/1991 | Chin et al. |
| 5,006,110 | A | 4/1991 | Garrison et al. |
| 5,020,535 | A | 6/1991 | Parker et al. |
| 5,026,387 | A | 6/1991 | Thomas |
| 5,032,939 | A | 7/1991 | Mihara et al. |
| 5,039,973 | A | 8/1991 | Carballo |
| 5,091,656 | A | 2/1992 | Gahn |
| 5,108,367 | A | 4/1992 | Epstein et al. |
| 5,110,270 | A | 5/1992 | Morrick |
| 5,125,891 | A | 6/1992 | Hossain et al. |
| 5,160,317 | A | 11/1992 | Costin |
| 5,195,960 | A | 3/1993 | Hossain et al. |
| 5,195,961 | A | 3/1993 | Takahashi et al. |
| 5,195,971 | A | 3/1993 | Takahashi et al. |
| 5,230,614 | A | 7/1993 | Zanger et al. |
| 5,242,404 | A | 9/1993 | Conley et al. |
| 5,249,121 | A | 9/1993 | Baum et al. |
| 5,267,956 | A | 12/1993 | Beuchat |
| 5,268,624 | A | 12/1993 | Zanger |
| 5,271,379 | A | 12/1993 | Phan et al. |
| 5,282,787 | A | 2/1994 | Wortrich |
| 5,323,543 | A | 6/1994 | Steen et al. |
| 5,342,293 | A | 8/1994 | Zanger |
| 5,350,357 | A | 9/1994 | Kamen et al. |
| 5,351,676 | A | 10/1994 | Putman |
| 5,354,268 | A | 10/1994 | Peterson et al. |
| 5,378,126 | A | 1/1995 | Abrahamson et al. |
| 5,388,569 | A | 2/1995 | Kepley |
| 5,429,601 | A | 7/1995 | Conley et al. |
| 5,454,783 | A | 10/1995 | Grieshaber et al. |
| 5,464,391 | A | 11/1995 | Devale |
| 5,470,211 | A | 11/1995 | Knott et al. |
| 5,470,312 | A | 11/1995 | Zanger et al. |
| 5,499,969 | A | 3/1996 | Beuchat et al. |
| 5,520,652 | A * | 5/1996 | Peterson ............ 604/119 |
| 5,533,976 | A | 7/1996 | Zaleski et al. |
| 5,549,461 | A | 8/1996 | Newland |
| 5,554,894 | A | 9/1996 | Sepielli |
| 5,561,575 | A | 10/1996 | Eways |
| 5,569,188 | A | 10/1996 | MacKool |
| 5,580,347 | A | 12/1996 | Reimels |
| 5,591,127 | A | 1/1997 | Barwick, Jr. et al. |
| 5,653,887 | A | 8/1997 | Wahl et al. |
| 5,657,000 | A | 8/1997 | Ellingboe |
| 5,676,530 | A | 10/1997 | Nazarifar |
| 5,676,649 | A | 10/1997 | Boukhny et al. |
| 5,676,650 | A | 10/1997 | Grieshaber et al. |
| 5,693,020 | A | 12/1997 | Rauh |
| 5,697,898 | A * | 12/1997 | Devine ............ 604/22 |
| 5,697,910 | A | 12/1997 | Cole et al. |
| 5,700,240 | A | 12/1997 | Barwick, Jr. et al. |
| 5,724,264 | A | 3/1998 | Rosenberg et al. |
| 5,728,130 | A | 3/1998 | Ishikawa et al. |
| 5,733,256 | A * | 3/1998 | Costin ............ 604/22 |
| 5,733,263 | A | 3/1998 | Wheatman |
| 5,745,647 | A | 4/1998 | Krause |
| 5,746,713 | A | 5/1998 | Hood et al. |
| 5,747,824 | A | 5/1998 | Jung et al. |
| 5,752,918 | A | 5/1998 | Fowler et al. |
| 5,777,602 | A | 7/1998 | Schaller et al. |
| 5,805,998 | A | 9/1998 | Kodama |
| 5,807,075 | A | 9/1998 | Jacobsen et al. |
| 5,810,765 | A | 9/1998 | Oda |
| 5,810,766 | A | 9/1998 | Barnitz et al. |
| 5,830,176 | A | 11/1998 | MacKool |
| 5,843,109 | A | 12/1998 | Mehta et al. |
| 5,859,642 | A | 1/1999 | Jones |
| 5,871,492 | A | 2/1999 | Sorensen |
| 5,879,298 | A | 3/1999 | Drobnitzky et al. |
| 5,883,615 | A | 3/1999 | Fago et al. |
| 5,899,674 | A | 5/1999 | Jung et al. |
| 5,928,257 | A | 7/1999 | Kablik et al. |
| 5,938,655 | A | 8/1999 | Bisch et al. |
| 5,983,749 | A | 11/1999 | Holtorf |
| 6,002,484 | A | 12/1999 | Rozema et al. |
| 6,024,428 | A | 2/2000 | Uchikata |
| 6,028,387 | A | 2/2000 | Boukhny |
| 6,062,829 | A | 5/2000 | Ognier |
| 6,077,285 | A | 6/2000 | Boukhny |
| 6,086,598 | A | 7/2000 | Appelbaum et al. |
| 6,109,895 | A | 8/2000 | Ray et al. |
| 6,117,126 | A | 9/2000 | Appelbaum et al. |
| 6,139,320 | A | 10/2000 | Hahn |
| 6,150,623 | A | 11/2000 | Chen |
| 6,159,175 | A | 12/2000 | Strukel et al. |
| 6,179,829 | B1 | 1/2001 | Bisch et al. |
| 6,200,287 | B1 | 3/2001 | Keller et al. |
| 6,219,032 | B1 | 4/2001 | Rosenberg et al. |
| 6,251,113 | B1 | 6/2001 | Appelbaum et al. |
| 6,258,111 | B1 | 7/2001 | Ross et al. |
| 6,260,434 | B1 | 7/2001 | Holtorf |
| 6,360,630 | B2 | 3/2002 | Holtorf |
| 6,368,269 | B1 | 4/2002 | Lane |
| 6,411,062 | B1 | 6/2002 | Baranowski et al. |
| 6,424,124 | B2 | 7/2002 | Ichihara et al. |
| 6,436,072 | B1 | 8/2002 | Kullas et al. |
| 6,452,120 | B1 | 9/2002 | Chen |
| 6,452,123 | B1 | 9/2002 | Chen |
| 6,491,661 | B1 | 12/2002 | Boukhny et al. |
| 6,511,454 | B1 | 1/2003 | Nakao et al. |
| 6,537,445 | B2 | 3/2003 | Muller |
| 6,561,999 | B1 | 5/2003 | Nazarifar et al. |
| 6,595,948 | B2 | 7/2003 | Suzuki et al. |
| 6,632,214 | B2 | 10/2003 | Morgan et al. |
| 6,674,030 | B2 | 1/2004 | Chen et al. |
| 6,780,166 | B2 | 8/2004 | Kanda et al. |
| 6,830,555 | B2 | 12/2004 | Rockley et al. |
| 6,852,092 | B2 | 2/2005 | Kadziauskas et al. |
| 6,862,951 | B2 | 3/2005 | Peterson et al. |
| 6,908,451 | B2 | 6/2005 | Brody et al. |
| 6,962,488 | B2 | 11/2005 | Davis et al. |
| 6,962,581 | B2 | 11/2005 | Thoe |
| 6,986,753 | B2 | 1/2006 | Bui |
| 7,011,761 | B2 | 3/2006 | Muller |
| 7,012,203 | B2 | 3/2006 | Hanson et al. |
| 7,070,578 | B2 | 7/2006 | Leukanech et al. |
| 7,073,083 | B2 | 7/2006 | Litwin, Jr. et al. |
| 7,087,049 | B2 | 8/2006 | Nowlin et al. |
| 7,103,344 | B2 | 9/2006 | Menard |
| 7,167,723 | B2 | 1/2007 | Zhang |
| 7,168,930 | B2 | 1/2007 | Cull et al. |
| 7,169,123 | B2 | 1/2007 | Kadziauskas et al. |
| 7,236,766 | B2 | 6/2007 | Freeburg |
| 7,236,809 | B2 | 6/2007 | Fischedick et al. |
| 7,242,765 | B2 | 7/2007 | Hairston |
| 7,244,240 | B2 | 7/2007 | Nazarifar et al. |
| 7,289,825 | B2 | 10/2007 | Fors et al. |
| 7,300,264 | B2 | 11/2007 | Souza |
| 7,316,664 | B2 | 1/2008 | Kadziauskas et al. |
| 7,336,976 | B2 | 2/2008 | Ito |
| 7,381,917 | B2 | 6/2008 | Dacquay et al. |

(56) References Cited

U.S. PATENT DOCUMENTS

| | | |
|---|---|---|
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,785,316 B2 | 8/2010 | Claus et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 8,157,792 B2 | 4/2012 | Dolliver et al. |
| 9,033,940 B2 | 5/2015 | Muri et al. |
| 9,658,468 B2 | 5/2017 | Dai |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0004657 A1 | 1/2002 | Morgan et al. |
| 2002/0007671 A1 | 1/2002 | Lavi et al. |
| 2002/0019215 A1 | 2/2002 | Romans |
| 2002/0019607 A1* | 2/2002 | Bui ............................ 604/67 |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0050619 A1* | 3/2003 | Mooijman et al. ........... 604/500 |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0019313 A1 | 1/2004 | Childers et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0097868 A1 | 5/2004 | Kadziauskas et al. |
| 2004/0127840 A1 | 7/2004 | Gara et al. |
| 2004/0193182 A1 | 9/2004 | Yaguchi et al. |
| 2004/0212344 A1 | 10/2004 | Tamura et al. |
| 2004/0215127 A1* | 10/2004 | Kadziauskas et al. ......... 604/22 |
| 2004/0224641 A1 | 11/2004 | Sinn |
| 2004/0253129 A1 | 12/2004 | Sorensen et al. |
| 2004/0267136 A1 | 12/2004 | Yaguchi et al. |
| 2005/0039567 A1 | 2/2005 | Peterson et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209552 A1 | 9/2005 | Beck et al. |
| 2005/0209560 A1 | 9/2005 | Boukhny et al. |
| 2005/0228266 A1 | 10/2005 | McCombs |
| 2005/0236936 A1 | 10/2005 | Shiv et al. |
| 2005/0245888 A1 | 11/2005 | Cull |
| 2005/0261628 A1 | 11/2005 | Boukhny et al. |
| 2005/0267504 A1 | 12/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1* | 4/2006 | Holden ..................... 417/477.2 |
| 2006/0114175 A1 | 6/2006 | Boukhny |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0248477 A1 | 10/2007 | Nazarifar et al. |
| 2007/0249942 A1 | 10/2007 | Salehi et al. |
| 2007/0252395 A1 | 11/2007 | Williams et al. |
| 2007/0287959 A1 | 12/2007 | Walter et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0082040 A1 | 4/2008 | Kubler et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1* | 5/2008 | Muri ................... A61F 9/00745 604/294 |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125694 A1 | 5/2008 | Domash |
| 2008/0125695 A1* | 5/2008 | Hopkins et al. ................ 604/35 |
| 2008/0125697 A1* | 5/2008 | Gao ............................... 604/35 |
| 2008/0125698 A1* | 5/2008 | Gerg et al. ...................... 604/35 |
| 2008/0129695 A1 | 6/2008 | Li |
| 2008/0146989 A1 | 6/2008 | Zacharias |
| 2008/0200878 A1 | 8/2008 | Davis et al. |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0087327 A1 | 4/2009 | Voltenburg, Jr. et al. |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0057016 A1 | 3/2010 | Dale et al. |
| 2010/0069825 A1 | 3/2010 | Raney |
| 2010/0069828 A1 | 3/2010 | Steen et al. |
| 2010/0140149 A1 | 6/2010 | Fulkerson et al. |
| 2010/0152685 A1 | 6/2010 | Goh |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2011/0208047 A1 | 8/2011 | Fago |
| 2011/0251569 A1 | 10/2011 | Turner et al. |
| 2012/0065580 A1 | 3/2012 | Gerg et al. |
| 2012/0078181 A1 | 3/2012 | Smith et al. |
| 2012/0083735 A1 | 4/2012 | Pfouts |
| 2012/0083736 A1 | 4/2012 | Pfouts et al. |
| 2012/0083800 A1 | 4/2012 | Andersohn |
| 2013/0072853 A1 | 3/2013 | Wong et al. |
| 2013/0169412 A1 | 7/2013 | Roth |
| 2013/0184676 A1 | 7/2013 | Kamen et al. |
| 2013/0245543 A1 | 9/2013 | Gerg et al. |
| 2013/0267892 A1 | 10/2013 | Woolford et al. |

(56) References Cited

U.S. PATENT DOCUMENTS

| | | |
|---|---|---|
| 2013/0289475 A1 | 10/2013 | Muri et al. |
| 2013/0303978 A1 | 11/2013 | Ross |
| 2013/0336814 A1 | 12/2013 | Kamen et al. |
| 2014/0178215 A1 | 6/2014 | Baxter et al. |
| 2014/0188076 A1 | 7/2014 | Kamen et al. |
| 2014/0276424 A1 | 9/2014 | Davis et al. |
| 2016/0151564 A1 | 6/2016 | Magers et al. |

FOREIGN PATENT DOCUMENTS

| | | |
|---|---|---|
| DE | 3826414 A1 | 2/1989 |
| EP | 56019 A1 | 7/1982 |
| EP | 424687 A1 | 5/1991 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | 57024482 A | 2/1982 |
| JP | S58167333 A | 10/1983 |
| JP | S62204463 A | 9/1987 |
| JP | 2005195653 A | 7/2005 |
| JP | 2008188110 A | 8/2008 |
| WO | 9220310 A1 | 11/1992 |
| WO | WO-9315777 A2 | 8/1993 |
| WO | WO-9317729 A1 | 9/1993 |
| WO | WO-9324082 A1 | 12/1993 |
| WO | WO-9405346 A1 | 3/1994 |
| WO | 96/32144 | 10/1996 |
| WO | 9737700 A1 | 10/1997 |
| WO | WO-9818507 A1 | 5/1998 |
| WO | WO-9917818 A1 | 4/1999 |
| WO | 0000096 A1 | 1/2000 |
| WO | WO-0070225 A1 | 11/2000 |
| WO | WO-0122696 A1 | 3/2001 |
| WO | 0226286 A2 | 4/2002 |
| WO | WO-0228449 A2 | 4/2002 |
| WO | WO-0234314 A1 | 5/2002 |
| WO | WO-03102878 A1 | 12/2003 |
| WO | WO-04096360 A1 | 11/2004 |
| WO | WO-2004114180 A1 | 12/2004 |
| WO | WO-05084728 A2 | 9/2005 |
| WO | 05092047 A2 | 10/2005 |
| WO | WO-05092023 A2 | 10/2005 |
| WO | 06101908 A2 | 9/2006 |
| WO | 06125280 A1 | 11/2006 |
| WO | 2007121144 A1 | 10/2007 |
| WO | 2007143797 A1 | 12/2007 |
| WO | WO-2007143677 A2 | 12/2007 |
| WO | WO-2007149637 A2 | 12/2007 |
| WO | 2008030872 A1 | 3/2008 |
| WO | 2008060995 A1 | 5/2008 |
| WO | WO-2008060859 A1 | 5/2008 |
| WO | WO-2008060902 A1 | 5/2008 |
| WO | 2009123547 A1 | 10/2009 |
| WO | 2010054146 A1 | 5/2010 |
| WO | 2010054225 A2 | 5/2010 |
| WO | 2010151704 A1 | 12/2010 |
| WO | 2012151062 A1 | 11/2012 |
| WO | WO-2013142009 A1 | 9/2013 |
| WO | 2015009945 A1 | 1/2015 |

OTHER PUBLICATIONS

European Search Report for Application No. EP10164058, dated Jun. 25, 2010, 2 pages.

European Search Report for Application No. EP13184138.9, dated Oct. 24, 2013, 7 pages.

Examination Report dated Mar. 28, 2012 for European Application No. EP09791072 filed Jul. 31, 2009, 3 pages.

International Preliminary Report on Patentability and Written Opinion for Application No. PCT/US07/083880, dated May 12, 2009, 7 pages.

International Preliminary Report on Patentability and Written Opinion for Application No. PCT/US07/084163, dated May 12, 2009, 8 pages.

International Preliminary Report on Patentability and Written Opinion for Application No. PCT/US08/064240, dated Nov. 24, 2009, 7 pages.

International Preliminary Report on Patentability and Written Opinion for Application No. PCT/US2006/38978, dated Apr. 16, 2008, 8 pages.

International Preliminary Report on Patentability and Written Opinion for Application No. PCT/US2006/39868, dated Apr. 16, 2008, 6 pages.

International Preliminary Report on Patentability and Written Opinion for Application No. PCT/US2008/072974, dated Feb. 16, 2010, 6 pages.

International Preliminary Report on Patentability and Written Opinion for Application No. PCT/US2009/052473, dated Feb. 1, 2011, 7 pages.

International Preliminary Report on Patentability and Written Opinion for Application No. PCT/US2009/063479, dated May 10, 2011, 11 pages.

International Preliminary Report on Patentability and Written Opinion for Application No. PCT/US2009/063589, dated May 10, 2011, 12 pages.

International Search Report and Written Opinion for Application No. PCT/US2014/047055, dated Oct. 17, 2014, 11 pages.

International Search Report and Written Opinion, dated Mar. 2, 2010, and International Preliminary Report on Patentability, dated May 10, 2011, for Application No. PCT/US2009/063482, 13 pages.

International Search Report and Written Opinion, dated Nov. 2, 2009, and International Preliminary Report on Patentability, dated Feb. 1, 2011, for Application No. PCT/US2009/052466, 12 pages.

International Search Report and Written Opinion, dated May 10, 2010, and International Preliminary Report on Patentability, dated May 10, 2011, for Application No. PCT/US2009/063569, 17 pages.

International Search Report and Written Opinion, dated Feb. 11, 2010, and International Preliminary Report on Patentability, dated May 10, 2011, for Application No. PCT/US2009/063486, 13 pages.

International Search Report for Application No. PCT/US2006/38978, dated Feb. 27, 2007, 3 pages.

International Search Report for Application No. PCT/US2006/39868, dated Nov. 12, 2007, 3 pages.

International Search Report for Application No. PCT/US2009/063479, dated Jun. 11, 2010, 5 pages.

International Search Report for Application No. PCT/US2009/063589, dated Jul. 21, 2010, 7 pages.

International Search Report for Application No. PCT/US2013/027728, dated Jul. 31, 2013, 9 pages.

Merritt R., et al., Wireless Nets Starting to link Medical Gear [online] 2004 [retrieved on Feb. 12, 2007]. Retrieved from the Internet: <http://www.embedded.com/news/embeddedindustry/17200577?_requestid=174370>.

International Search Report and Written Opinion for Application No. PCT/US2016/049970, dated Dec. 5, 2016, 12 pages.

(56) References Cited

OTHER PUBLICATIONS

International Search Report and Written Opinion for Application No. PCT/US2015/066036, dated Jul. 4, 2016, 20 pages.
International Search Report and Written Opinion for Application No. PCT/US2016/061648, dated Feb. 7, 2017, 12 pages.
Boyd, "Preparing for the Transition" in: The Art and the Science of Cataract Surgery, Chapter 7, 2001, pp. 93-133.
Clo-pending U.S. Appl. No. 13/922475, filed Jun. 20, 2013.
English Human Translation of JP57024482 from Feb. 9, 1982.
International Preliminary Report on Patentability and Written Opinion for Application No. PCT/US07/083875, dated May 12, 2009, 8 pages.
International Preliminary Report on Patentability and Written Opinion for Application No. PCT/US07/084157, dated May 12, 2009, 10 pages.
International Search Report for Application No. PCT/US07/083875, dated May 7, 2008, 4 pages.
International Search Report for Application No. PCT/US07/083880, dated May 30, 2008, 4 pages.
International Search Report for Application No. PCT/US07/084157, dated Apr. 1, 2008, 3 pages.
International Search Report for Application No. PCT/US07/084163, dated Apr. 1, 2008, 3 pages.
International Search Report for Application No. PCT/US08/064240, dated Oct. 29, 2008, 3 pages.
International Search Report for Application No. PCT/US08/071704, dated Nov. 26, 2008, 3 pages.
International Search Report for Application No. PCT/US08/072974, dated Feb. 23, 2009, 2 pages.
International Search Report for Application No. PCT/US2009/052473, dated Nov. 2, 2009, 3 pages.

\* cited by examiner

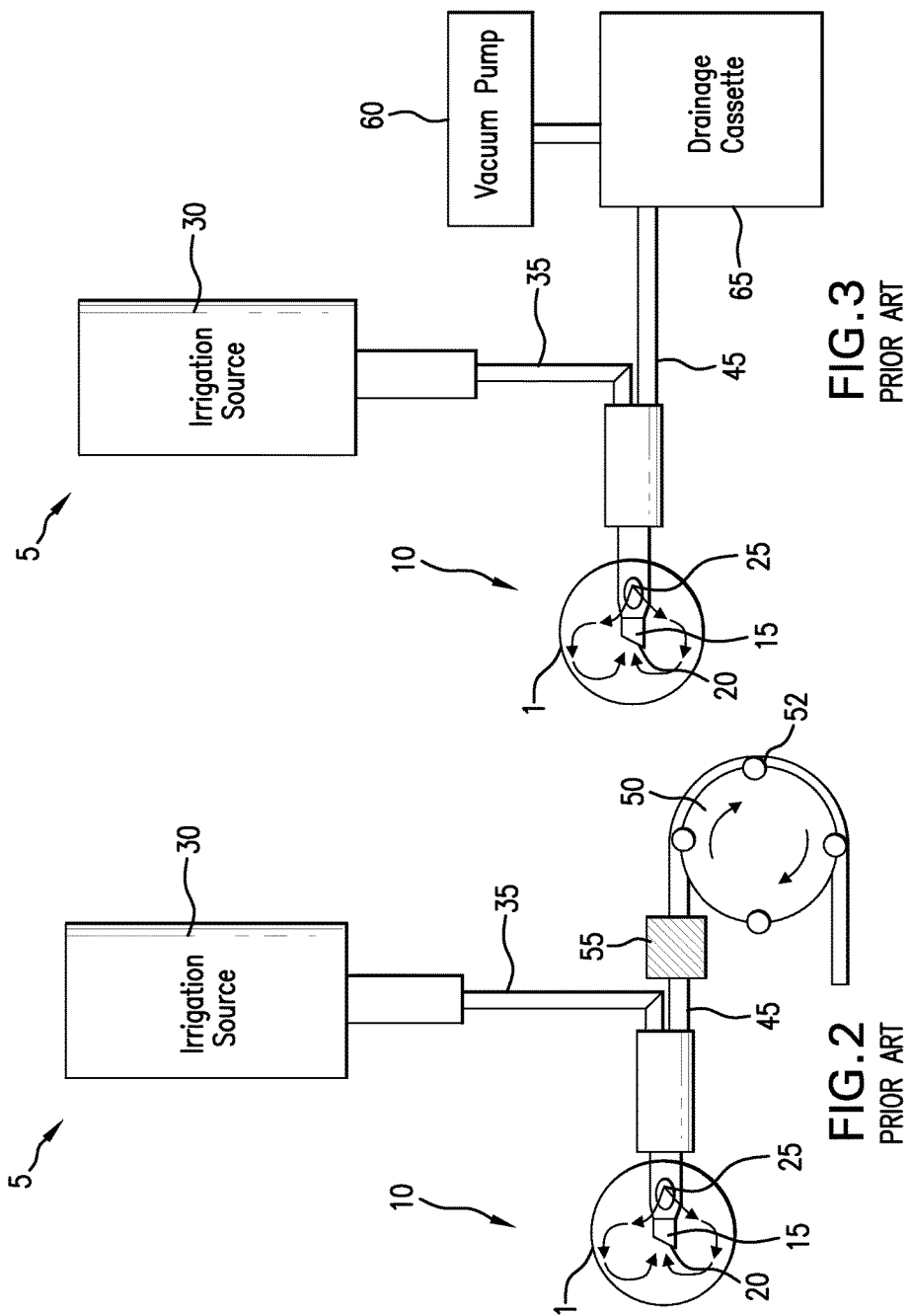

SYSTEMS AND METHODS FOR PHACOEMULSIFICATION WITH VACUUM BASED PUMPS

FIELD OF THE INVENTION

The field of the invention relates to systems and methods for ophthalmic surgery, and more particularly to systems and methods for phacoemulsification with vacuum-based aspiration pumps.

BACKGROUND OF THE INVENTION

A number of medically recognized techniques are utilized for crystalline lens removal based on a variety of technologies, for example, phacoemulsification, mechanical cutting or destruction, laser, water, and so on.

The phacoemulsification method includes making a corneal and/or scleral incision and the insertion of a phacoemulsification handpiece which includes a needle that is ultrasonically driven in order to emulsify, or liquefy, the lens. A phacoemulsification system 5 known in the art is shown in FIG. 1. The system 5 generally includes a phacoemulsification handpiece 10 coupled to an irrigation source 30 and an aspiration pump 40. The handpiece 10 includes a distal tip 15 (shown within the anterior chamber of the patient's eye 1) that emits ultrasonic energy to emulsify the crystalline lens within the patient's eye 1. The handpiece 10 further includes an irrigation port 25 proximal to the distal tip 15, which is coupled to an irrigation source 30 via an irrigation line 35, and an aspiration port 20 at the distal tip 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified crystalline lens material are aspiration from the eye 1 by the aspiration pump 40 via the aspiration port 20 and the aspiration line 45. Other medical techniques for removing crystalline lenses also typically include irrigating the eye and aspirating lens parts and other liquids. Additionally, some procedures may include irrigating the eye 1 and aspirating the irrigating fluid without concomitant destruction, alteration or removal of the lens.

Aspiration can be achieved with a variety of different aspiration pumps 40 known in the art. The two most common types are (1) volumetric flow or positive displacement pumps (such as peristaltic or scroll pumps) and (2) vacuum-based pumps (such as venturi, diaphragm, or rotary-vane pumps). Each type has its own general advantages and disadvantages. Turning to FIG. 2, an example peristaltic flow pump 50 is illustrated. In this configuration, the aspiration line 45 is in direct contact with a rotating pump head 50 having rollers 52 around its perimeter. As the pump head 50 rotates clockwise, the rollers 52 press against the line 45 causing fluid to flow within the line 45 in the direction of the rollers 52. This is referred to as a volumetric flow pump because the pump 50 directly controls the volume or rate of fluid flow. An advantage with this type of pump 50 is that the rate of fluid flow can be easily and precisely controlled by adjusting the rotational speed of the pump head 50.

Turning to FIG. 3, an example vacuum-based pump 60 is illustrated. This type of pump indirectly controls fluid flow by controlling the vacuum within the fluidic circuit. For example, the vacuum-based pump 60 can be a pneumatic pump (e.g., a venturi pump) that creates a lower pressure in a drainage cassette reservoir 65 that causes the fluid to flow from the eye into the aspiration line 45 and into the drainage cassette reservoir 65. Thus, instead of pushing fluid through the aspiration line 45 like the flow pump 50, the fluid is essentially pulled by vacuum through the line 45. The rate of fluid flow generated by a vacuum-based pump is generally higher than the rate of fluid flow generated by a volumetric flow based pump; however, current systems and methods for controlling the rate of volumetric flow for the vacuum-based pump, which typically involve manually adjusting the operative vacuum level, are imprecise, which raises safety and efficacy concerns.

As is well known, for these various surgical techniques it is necessary to maintain a stable volume of liquid in the anterior chamber of the eye and this is accomplished by irrigating fluid into the eye at the same rate as aspirating fluid and lens material. For example, see U.S. Pat. No. 5,700,240, to Barwick et. al, filed Jan. 24, 1995 ("Barwick") and U.S. patent application Ser. No. 11/401,529 to Claus et. al, filed Apr. 10, 2006 ("Claus"), which are both hereby incorporated by reference in their entirety. During phacoemulsification, it is possible for the aspirating phacoemulsification handpiece 10 to become occluded. This occlusion is caused by particles blocking a lumen or tube in the aspirating handpiece 10, e.g., the aspiration port 20 or irrigation port 25. In the case of volumetric flow based pumps, this blockage can result in increased vacuum (i.e. increasingly negative pressure) in the aspiration line 45 and the longer the occlusion is in place, the greater the vacuum if the pump continues to run. In contrast, with a vacuum-based pump, this blockage can result in a volumetric fluid flow drop off near the aspiration port 20. In either case, once the occlusion is cleared, a resulting rush of fluid from the anterior chamber into the aspiration line 45 can outpace the volumetric flow of new fluid into the eye 1 from the irrigation source 30.

The resulting imbalance of incoming and outgoing fluid can create a phenomenon known as post-occlusion surge or fluidic surge, in which the fluid in the anterior chamber of the eye is removed faster than can be replaced. Such post-occlusion surge events may lead to eye trauma. The most common approach to preventing or minimizing the post-occlusion surge is to quickly adjust the vacuum-level or rate of fluid flow in the aspiration line 45 and/or the ultrasonic power of the handpiece 10 upon detection of an occlusion. Many surgeons rely on their own visual observations to detect the occlusion; however, because of the unpredictable and time-sensitive nature of the problem, a reliable computer-based detection and response system is preferable to provide a faster reaction time.

For current systems with volumetric flow pumps 50, if an occlusion occurs, the flow rate will decrease at the aspiration port 20 and the vacuum level within the aspiration line 45 between the pump 50 and the handpiece 10 will increase. Thus, a computer-based system (not shown) can utilize a vacuum sensor 55 placed on the aspiration line 45 to detect the vacuum increase and respond accordingly (an example of such a system is described in "Barwick" and "Claus"). For current systems with vacuum-based pumps 60, however, the vacuum level within the aspiration line 45 is tied to the vacuum power generated by the pump 60 and thus, may not be an effective indicator of whether an occlusion has occurred. Nonetheless, vacuum-based pumps may still be preferred in circumstances where high aspiration flow rate is desirable. Accordingly, an improved system and method for phacoemulsification having the advantages of both volume-based and vacuum-based pumps is desirable.

SUMMARY OF THE INVENTION

The invention is generally directed to systems and methods for ophthalmic surgery, and more particularly to systems and methods for phacoemulsification using vacuum-based aspiration pumps.

In accordance with one embodiment, a vacuum-based phacoemulsification system, having a handpiece, includes a subsystem to detect an occlusion occurring at the handpiece during operation.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 2 is a diagram of a phacoemulsification system having a volume-based or flow pump known in the art.

FIG. 3 is a diagram of a phacoemulsification system having a vacuum-based pump known in the art.

DETAILED DESCRIPTION OF THE PREFERRED EMBODIMENTS

What are described below are preferred embodiments of phacoemulsification systems utilizing vacuum-based aspiration systems, which can be applied to any system, medical or non-medical.

Figure 1:
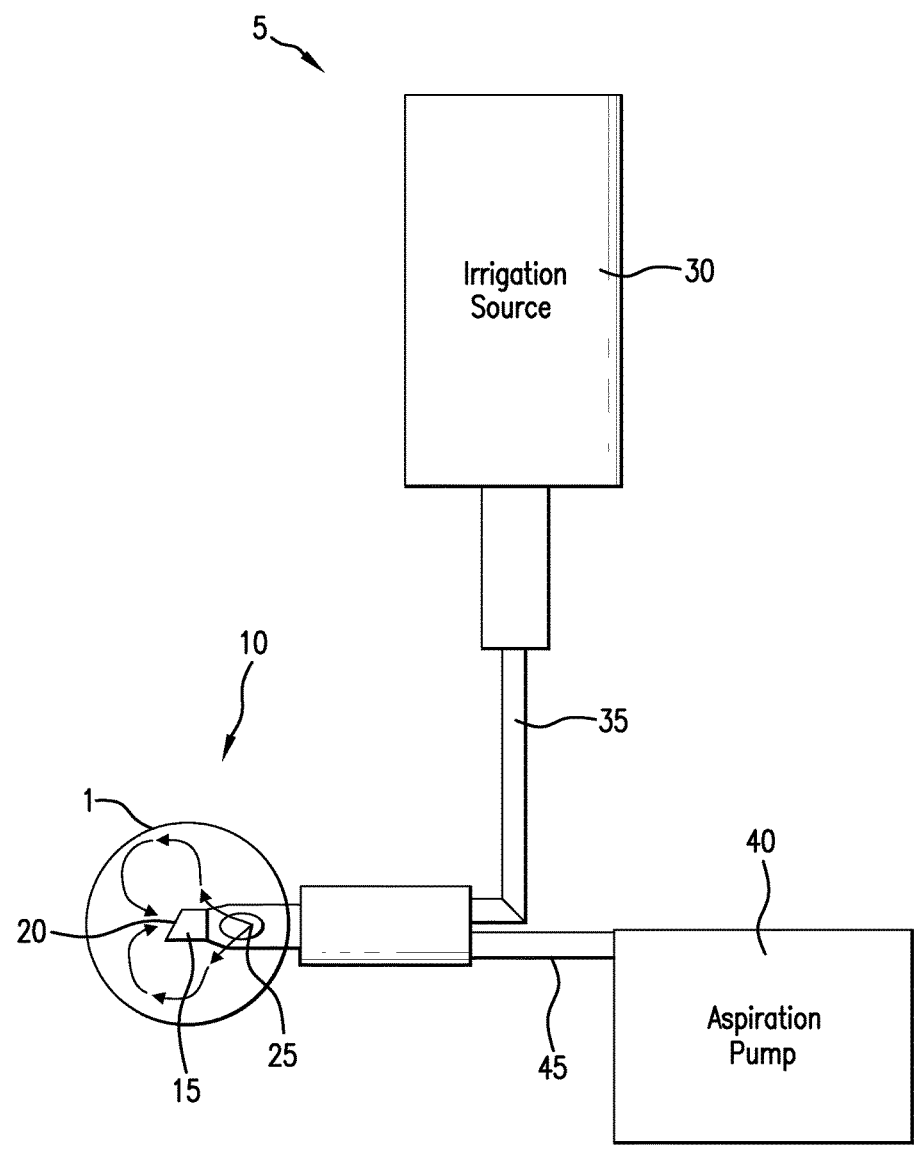
FIG. 1 is a diagram of a phacoemulsification system known in the art.
Figure 4:
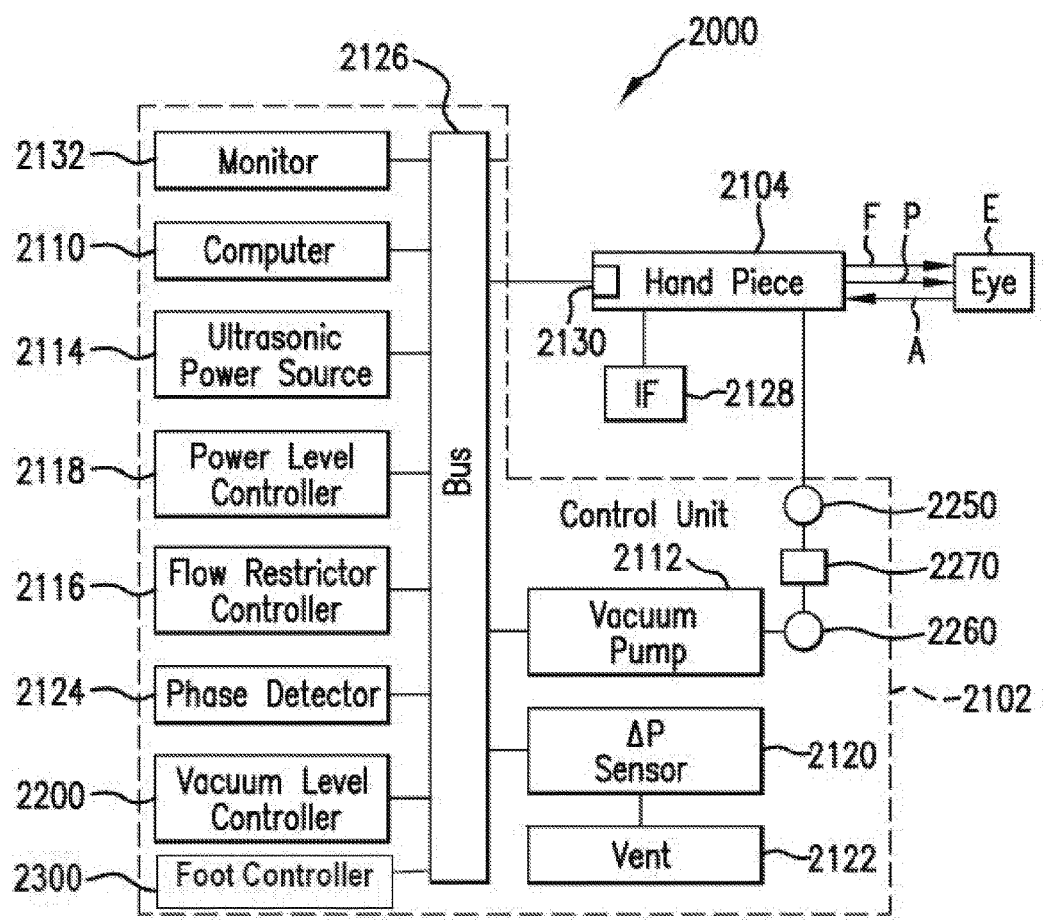
FIG. 4 is a diagram of a phacoemulsification system in accordance with a preferred embodiment.

Turning to FIG. 4, a functional block diagram of a phacoemulsification system in accordance with a preferred embodiment is shown. The system 2000 includes a control unit 2102 and a handpiece 2104 operably coupled together. The handpiece 2104 may include a needle (not shown) for insertion into an eye E and a vibrating unit (not shown) that is configured to ultrasonically vibrate the needle. The vibrating unit, which may include, e.g., a piezoelectric crystal, vibrates the needle according to one or more parameters, such as frequency, pulse width, shape, size, duty cycle, amplitude, and so on. The ultrasonic vibration is used to cut and emulsify the crystalline lens as is known in the art. Although the preferred embodiment described below include an ultrasonically vibrated needle, other methods and techniques for cutting and emulsifying the crystalline lens can be used, for example, a laser. The handpiece 2104 provides power, P, irrigation fluid, F, from an irrigation fluid ("IF") source 2128, and an aspiration line A. A phacoemulsification system having the irrigation line and the aspiration/ultrasonic power line coupled to separate handpieces respectively (also known in the industry as a "bi-manual" system, not shown) can also be used.

The control unit 2102 includes a dual pump system 2112 having vacuum and volume based pumps operative coupled to aspiration line A. As will be explained further below, the dual pump system 2112 enables a surgeon to toggle between either a vacuum-based pump or a volume based pump on demand during an operation, e.g., via a foot controller 2300, instead of limiting a surgeon to one or the other throughout the operation. The control unit 2102 further includes a microprocessor computer 2110 which is operably connected to and controls the various other elements of the system, such as the dual pump system 2112, a vacuum level controller 2200 to control the vacuum level of the vacuum-based pump when activated and a flow rate controller 2116 to control the flow rate of the volume-based pump when activated.

Other elements include a pulsed ultrasonic power source 2114 and an ultrasonic power level controller 2118 in accordance with algorithms described in the Claus application referenced above. The functional representation of the system 2000 also includes a system bus 2126 to enable the various elements to be operably in communication with each other.

Figure 5:
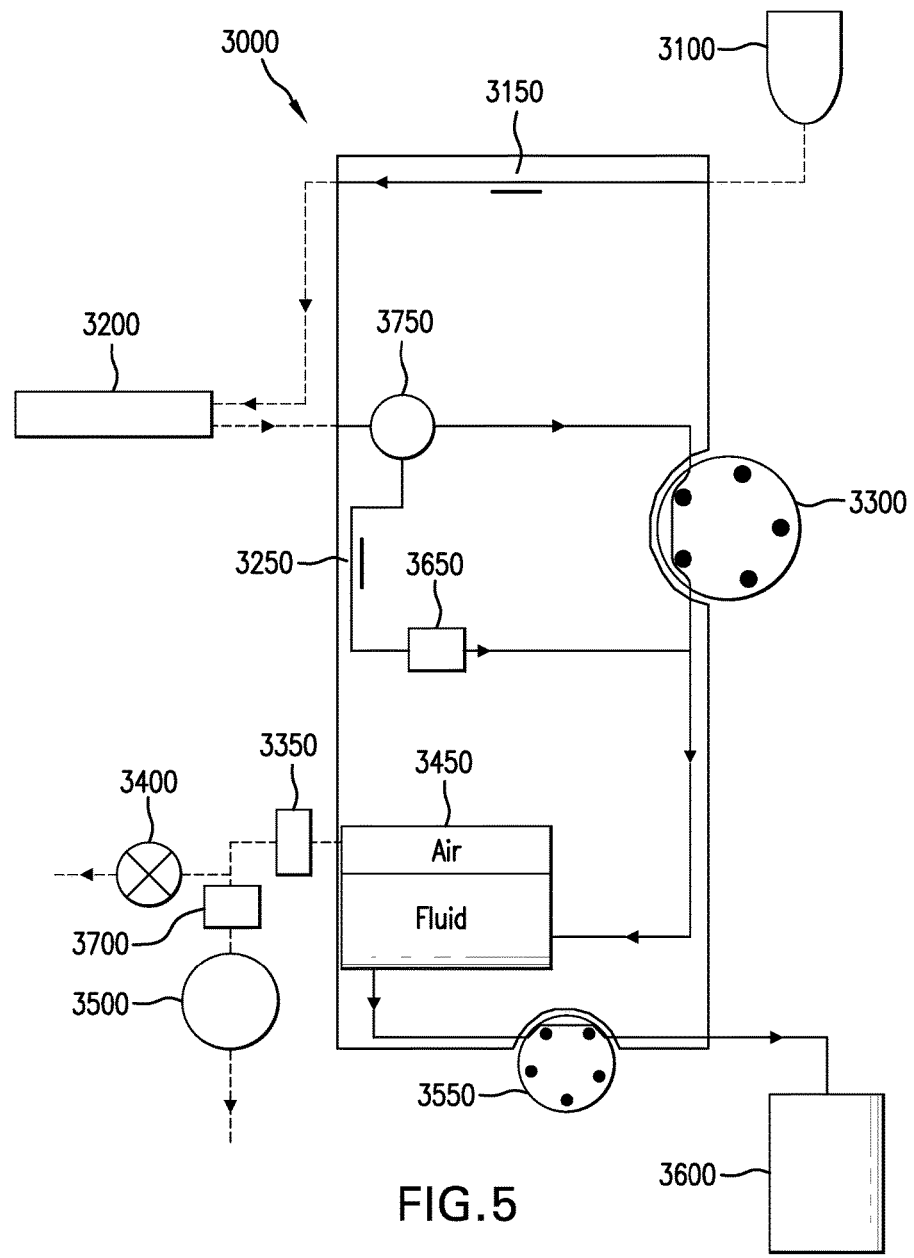
FIG. 5 is a diagram of an irrigation/aspiration system in accordance with a preferred embodiment.

Turning to FIG. 5, an irrigation/aspiration cassette 3000 (preferably disposable) is shown for use in a surgical system, such as a phacoemulsification system, e.g., 2000. As shown, the cassette 3000 supports a dual pump aspiration system, e.g., 2112 in FIG. 4 The irrigation/aspiration cassette 3000 is configured to be coupled to an irrigation source 3100 operatively coupled to a handpiece 2104 (also shown in FIG. 9) via an irrigation line. An irrigation valve 3150 controls the irrigation source 3100. The handpiece 2104 is further coupled to the aspiration portion of the cassette 3000, which is coupled to a dual pump system, e.g., 2112, having both a vacuum-based pump 3500 and a volume-based pump 3300. The operation of one pump or the other is controlled by a selector valve 3250, which can be operatively actuated by a controller 2102 and a foot controller 2300 known in the art, such as those set forth in U.S. Pat. No. 5,983,749, issued Nov. 16, 1999 for Duel Position Foot Pedal for Ophthalmic Surgery apparatus or U.S. patent application Ser. No. 09/140,874 filed Aug. 29, 1998 for Back Flip Medical Foot Pedal, which are both herein incorporated by reference in their entirety. The selector valve 3250 can be any type of actuator or valve known in the art, such as a mechanical actuator (e.g., a linear motor, axial solenoid, rotary solenoid, or electro magnetic motor), a pneumatic actuator (e.g., such as a low friction pneumatic rotary or axial bladder/cylinder with a variable pressure supply) or a thermal actuator (e.g., such as a bi-metallic strip).

When the selector valve 3250 is closed, then the volume-based pump 3300, which is a first peristaltic pump 3300 in the present embodiment, aspirates the fluid from the handpiece 2104. The volume-based pump 3300 pushes the fluid to a holding tank 3450, which can then be drained to a collection bag 3600 by a second peristaltic pump 3550. A vacuum sensor, or pressure transducer, 3750 communicatively coupled to a computer system, e.g., 2102 in FIG. 4, is utilized between the volume-based pump 3300 and the handpiece 2104 to detect any change in vacuum level in the aspiration line, which can indicate a possible occlusion.

When the selector valve 3250 is open and the peristaltic pump 3300 is off, then the aspirant fluid flows through the circuit controlled by the vacuum-based pump 3500, which creates an air-vacuum in the holding tank 3450 that sucks the fluid from the handpiece 2104. The aspiration portion of the cassette 3000 further includes an air filter 3350 and a vent valve 3400, which are utilized by the volume-based pump 3300 and the vacuum-based pump 3500. As mentioned above, when the vacuum-based pump 3500 is in operation, it may be difficult to use the vacuum sensor 3750 to detect the occurrence of an occlusion at the handpiece 2104 because the sensor 3750 would be tied to the vacuum provided by the pump 3500, which would remain unchanged if an occlusion occurred. One approach to utilizing the vacuum sensor 3750 in a vacuum-based pump 3500 to detect the occlusion is described in U.S. patent application Ser. No. 11/530,306, filed Sep. 8, 2006, entitled "SYSTEMS AND METHODS FOR POWER AND FLOW RATE CONTROL," which is incorporate herein by reference in its entirety. Additionally, a pump component 3700 may be coupled to a vacuum based pump 3500 and may be any applicable component such as a filter, a sensor a reservoir or the like.

In the alternative, data from the sensor 3750 can be sampled with the selector valve closed 3250, which effectively isolates the sensor 3750 from the holding tank 3450 and vacuum-based pump 3500. If the handpiece 2104 is unoccluded when the valve 3250 is closed, then aspirant fluid from the eye will enter the aspiration line to reach equilibrium between the aspiration line and the eye, thereby increasing the pressure within the line, and the pressure reading from the sensor 3750 will be higher than that of the selected vacuum level, i.e., when the sensor 3750 indicates that the pressure increased after the valve closed 3250, then the handpiece is unoccluded. If, on the other hand, the handpiece is occluded, then the aspirant fluid will not be able to enter the aspiration line to reach equilibrium, and the pressure remains substantially unchanged after the valve 3250 closes. Thus, when the valve 3250 closes, the reading from the sensor 3750 could then indicate the occurrence or presence of a sustained occlusion.

Figure 6:
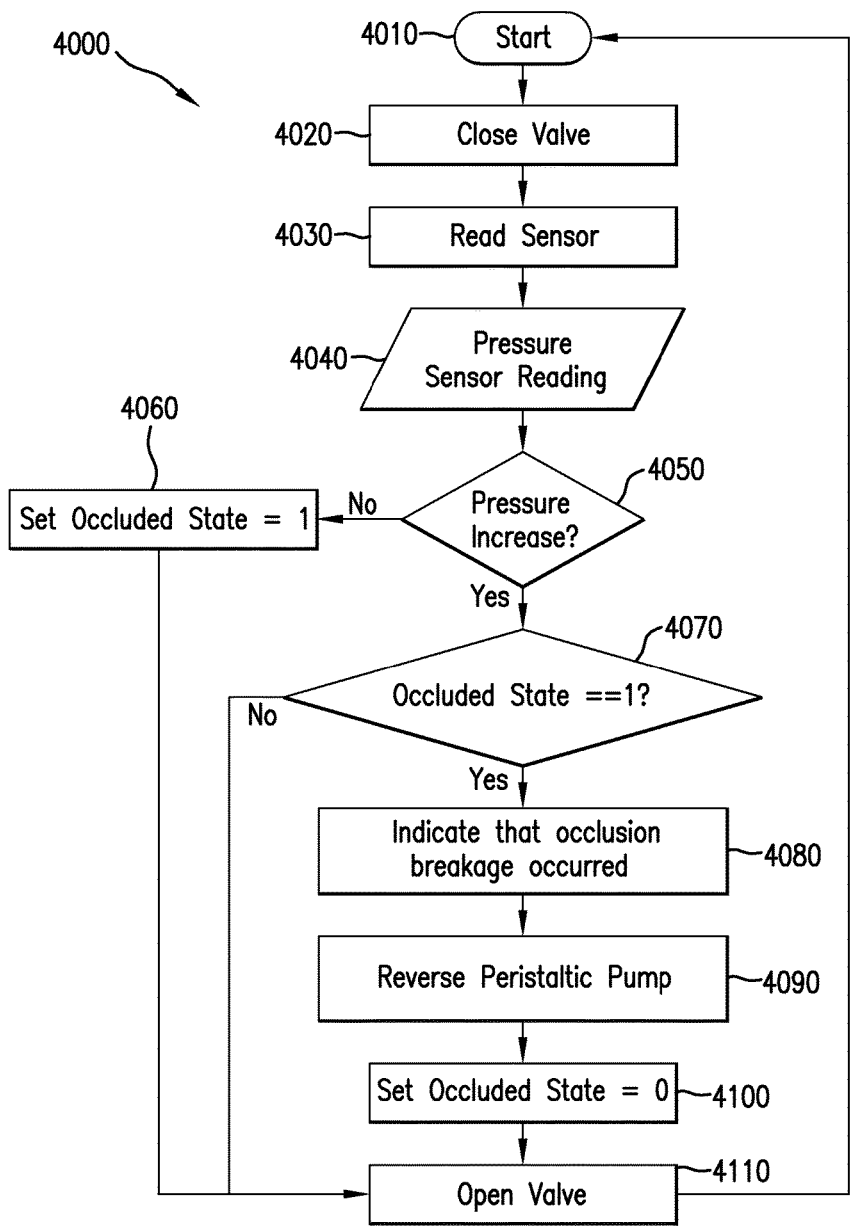
FIG. 6 is a flow chart of illustrating the operation of a vacuum-based phacoemulsification system in accordance with a preferred embodiment of the present invention.

Turning to FIG. 6, a flow chart is shown illustrating a method 4000 of detecting the onset, presence, breakage, and elimination of an occlusion in the handpiece 2104 when using the vacuum-based pump 3500 of a dual pump system 2112 having both vacuum-based and volume based pumps. The method could be implemented as a set of instruction on a computer readable medium within the controller 2102. In one implementation, a flag "occluded state" is stored, indicating whether the handpiece is occluded or not. At the beginning of the method 4000, the default value is zero (starting block 4010). To determine the presence of an occlusion, valve 3250 is closed, effectively isolating the vacuum pump 3500 from the handpiece 2104 and pressure sensor 3750 (action block 4020). The pressure sensor 3750 is then read by the controller 2102 (action block 4030). In a preferred embodiment, the pressure sensor 3750 is sampled or read multiple times, e.g., five (5) readings at 20 millisecond ("ms") intervals, thus creating a group or set of data (data block 4040) to calculate average values and/or upward/downward trends in pressure as a result of the valve 3250 being closed. As one of ordinary skill would appreciate, more sampling increases tolerance for error, which could be caused by environmental variables such as hysteresis. If the pressure sensor reading data (data block 4040) indicates that there's little or no change in the pressure after the valve 3250 is closed (decision block 4050), then that indicates the presence of an occlusion, thus, the occluded state flag is set to one (action block 4060). The onset of an occlusion could be indicated if the flag was zero prior to reaching this action block. The valve 3250 is then opened (action block 4110), and operation continues.

If the pressure sensor 3750 reading (data block 4040) indicates that there's been an increase in pressure after the valve 3250 is closed (decision block 4050), then that indicates that the handpiece 2104 is not occluded. If there was no occlusion in the last sampling, as indicated by the flag (decision block 4070), then the valve opens (action block 4110), and operation continues. If, however, there was an occlusion in the last sampling (decision block 4070), then that means the occlusion has broken (action block 4080). To prevent a post-occlusion surge, the controller 2102 can vent the aspiration line, either with the irrigation line (not shown), or, if a peristaltic pump 3300 is available, the peristaltic pump 3300 can be briefly reversed (action block 4090) to stabilize the aspiration line and counteract a potential surge. The occlusion state flag is then set to zero (action block 4100), valve 3250 is opened (action block 4110), and operation continues.

In a preferred embodiment, the sampling process 4000 occurs at a frequency and duration that quickly, accurately, and effectively detects the occurrence of an occlusion yet does not impede on the operation of the vacuum-based pump 3500, i.e., have little to no effect on the existing flow rate while the handpiece 2104 remains free of occlusion. This sampling process 4000 in conjunction with a computer-based algorithm, such as those described in the Claus and Barwick applications referenced above, enables the system 2000 to detect the onset, presence, breakage, or elimination of an occlusion, and respond accordingly when using a vacuum-based pump 3500, thereby preventing undesirable surge.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:
1. An intraocular lens removal device comprising:
 a handpiece;
 an aspiration line having a proximal end coupled to the handpiece and a distal end fluidly coupled to a holding tank;

a vacuum-based aspiration pump coupled to the holding tank, wherein the vacuum-based aspiration pump is selected from the group consisting of a venturi pump, a diaphragm pump, and a rotary-vane pump;

a vacuum level controller configured to control a vacuum level of the vacuum-based aspiration pump based on a selected vacuum level;

a pressure transducer coupled to the aspiration line between the handpiece and the holding tank;

a valve coupled to the aspiration line between the pressure transducer and the holding tank; and a computer controller communicatively coupled to the valve and the pressure transducer, wherein a processor of the computer controller periodically closes the valve, retrieves a pressure reading from the pressure transducer while the valve is closed, and determines whether the aspiration line is occluded based on a comparison of the selected vacuum level and the retrieved pressure reading.

2. The device of claim 1, wherein the aspiration line is further operatively coupled to a volume-based pump.

3. The device of claim 2, wherein, while the vacuum-based aspiration pump is in operation, the processor of the computer controller generates a signal to reverse the volume-based pump upon detecting an occlusion occurring within the aspiration line.

4. The device of claim 2, further comprising a foot controller operatively coupled to the computer controller, wherein the foot controller enables an operator to switch between operating the volume-based pump and the vacuum-based aspiration pump on demand during a lens removing procedure.

5. The device of claim 1, wherein, on a condition that the processor of the computer controller determines that the aspiration line is not occluded, the processor of the computer controller further determines whether the aspiration line was determined to be occluded in the last periodic reading of the pressure reading from the pressure transducer.

6. The device of claim 5, wherein, on a condition that the aspiration line was determined to be occluded in the last periodic reading of the pressure reading from the pressure transducer, venting the aspiration line to prevent a post-occlusion surge.

7. The device of claim 5, wherein the processor of the computer controller determines whether the aspiration line was determined to be occluded in the last periodic reading of the pressure reading from the pressure transducer by determining a value of a stored flag.

* * * * *